United States Patent [19]

Cassidy et al.

[11] 4,093,193

[45] June 6, 1978

[54] COMPOSITE HIGH TEMPERATURE PROTECTION TUBE

[75] Inventors: John E. Cassidy, Churchville; Max H. Kraus, Huntingdon Valley, both of Pa.

[73] Assignee: Electro-Nite Co., Philadelphia, Pa.

[21] Appl. No.: 804,417

[22] Filed: Jun. 7, 1977

[51] Int. Cl.$^2$ .......................... C21C 7/00; F16L 9/14; B65N 81/00
[52] U.S. Cl. ................................. 266/87; 266/225; 428/36; 138/141; 138/144; 156/190
[58] Field of Search ................ 428/36, 408, 438, 246, 428/450, 452, 538, 539; 156/190, 195; 138/144, 141, 177; 266/225, 226, 87

[56] References Cited

U.S. PATENT DOCUMENTS

| | | | |
|---|---|---|---|
| 3,036,929 | 5/1962 | Kawashima et al. | 138/141 |
| 3,430,940 | 3/1969 | Criss | 138/144 |
| 3,463,005 | 8/1969 | Hance | 266/87 |
| 3,830,173 | 8/1974 | Hubble et al. | 138/141 |

*Primary Examiner*—Douglas J. Drummond
*Attorney, Agent, or Firm*—Seidel, Gonda & Goldhammer

[57] ABSTRACT

The composite tube has an inner core of a first material, an intermediate zone of a second material surrounding said core, and an outer wrap surrounding and confining said intermediate zone. The intermediate zone is spirally wound layers of ceramic paper bonded together. The tube is light in weight and has a very low thermal conductivity.

13 Claims, 5 Drawing Figures

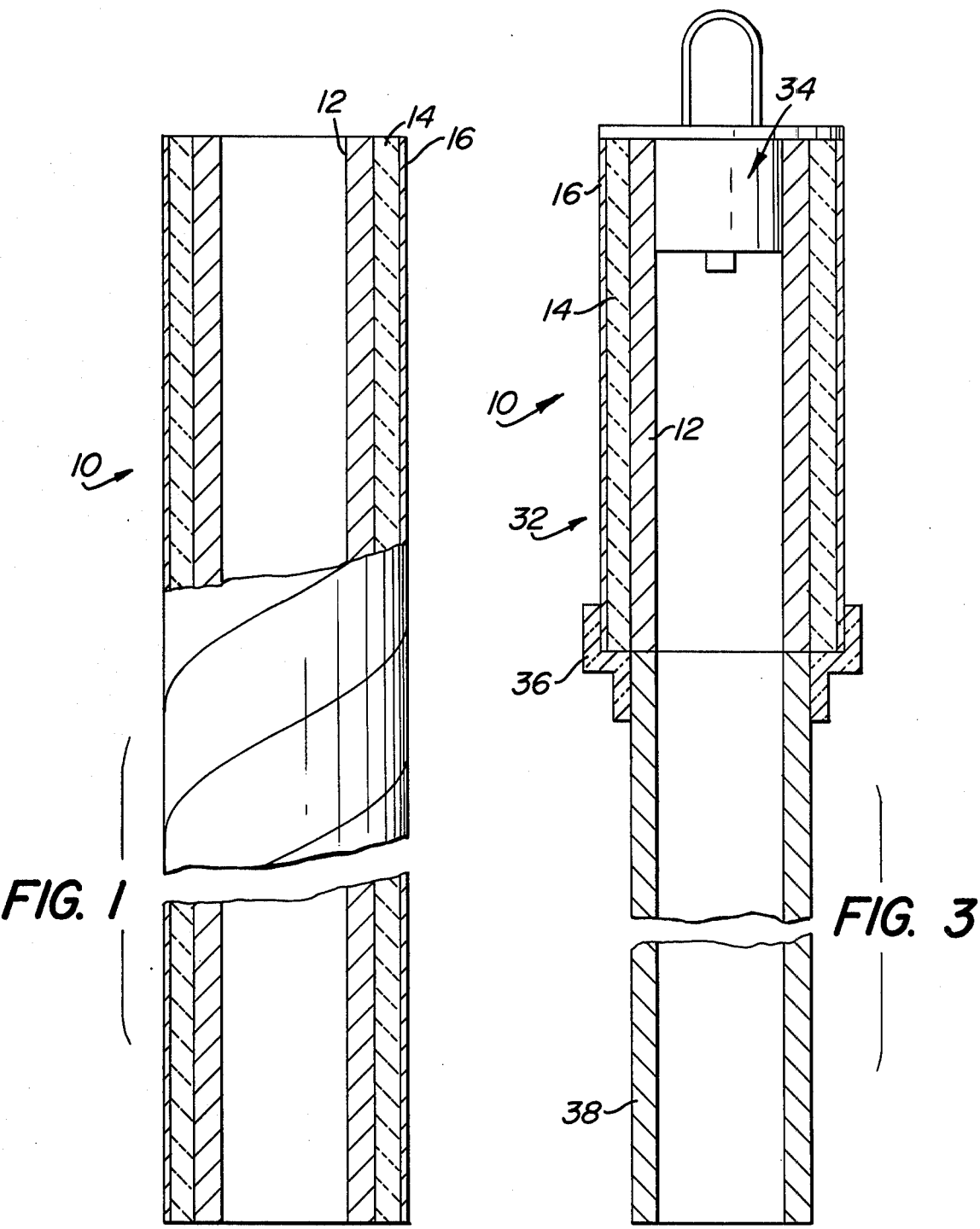

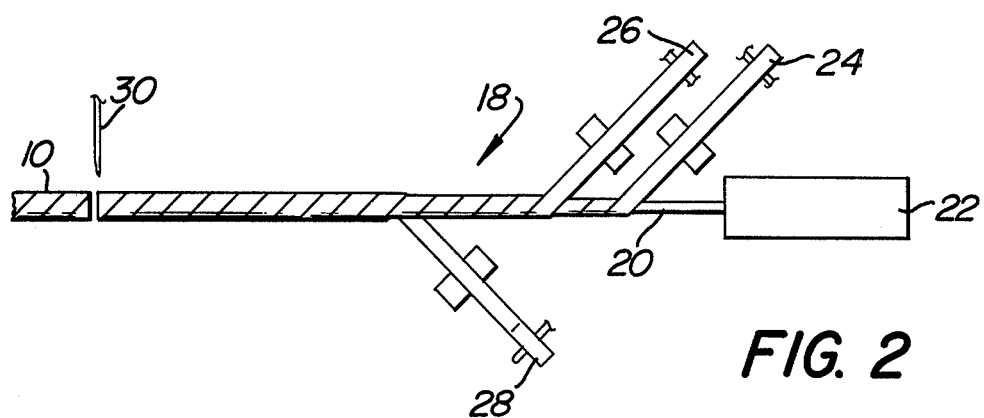
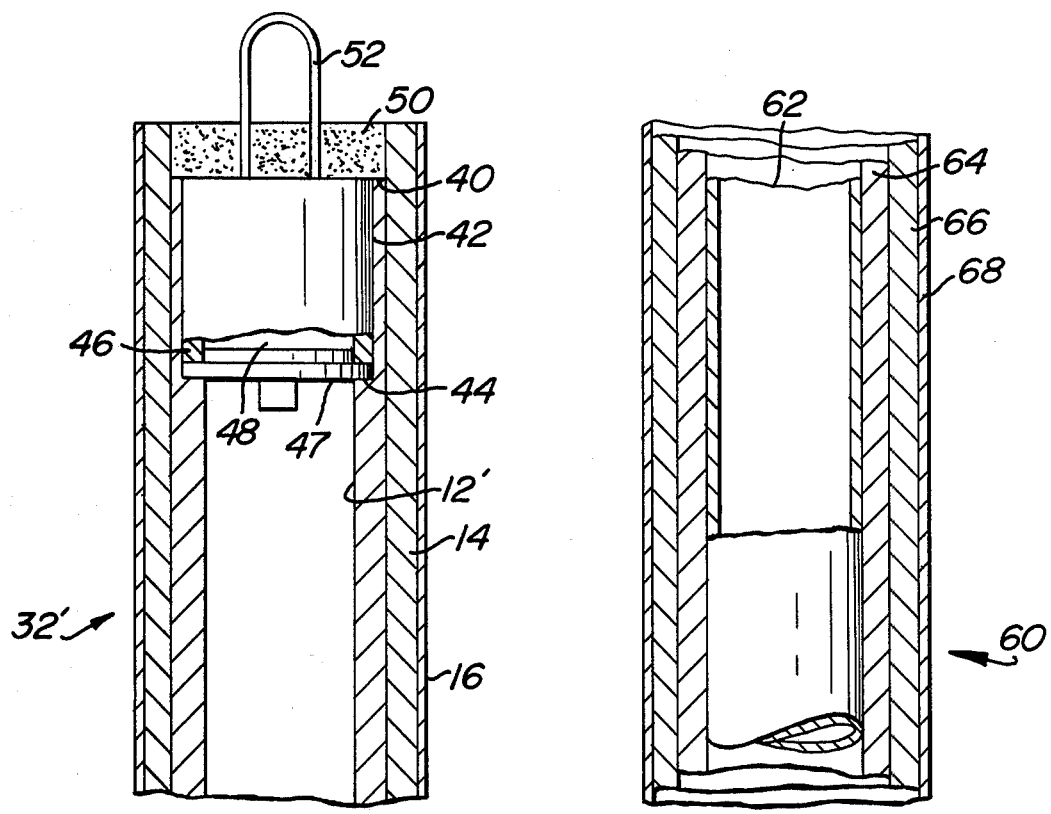

COMPOSITE HIGH TEMPERATURE PROTECTION TUBE

BACKGROUND

A large number of different high temperature protection tubes have been proposed heretofore. U.S. Pat. No. 3,816,183 discloses a high temperature protection tube of refractory fibers which have been vacuum-cast into the form of a sleeve. U.S. Pat. No. 3,398,027 discloses spiral windings of asbestos covered by a layer of refractory earth to prevent destruction of the layer of asbestos. Also, high temperature protection tubes are commercially available in the form of a ceramic paper having a plurality of wound superimposed layers to thereby form a hard, brittle tube.

A major problem with the high temperature protection tubes used heretofore is the initial cost of producing the tube. For example, ceramic paper tubes are produced by winding a web of paper having a width corresponding to the desired length of tubing onto a mandrel. The web is soaked with a bonding agent. The tube is manually removed from the mandrel, and then the tube is inserted into an oven where it is baked into a hard, brittle structure. The manufacturing steps for making ceramic paper tubes are slow and expensive.

As used herein, "ceramic paper" refers to paper made from ceramic or refractory fibers in the form of a sheet by a Fourdrinier processing machine. Ceramic papers are available commercially and typically examples are sold under the trademarks FIBERFRAX, KAOWOOL, etc. Ceramic paper has good chemical stability, high temperature stability, good stability or resistance to most chemicals, low thermal conductivity, light weight, thermal shock resistance, etc.

Due to the nature of ceramic paper, a substantial amount of time is required in order that superimposed layers will become bonded together. Initial efforts to use narrow strips of ceramic paper on a spiral tube machine were unsuccessful since the ceramic paper immediately sprung apart when removed off the mandrel.

SUMMARY OF THE INVENTION

The present invention is directed to a composite high temperature protection tube having an inner core of a first material which may be spirally wound paperboard, spirally wound aluminum foil, spirally wound plastic, a metal tube, etc. An intermediate zone surrounds the inner core and is preferably spirally wound layers of ceramic paper with juxtaposed layers bonded together. The ceramic paper is inorganic except for an organic binder in an amount sufficient to increase the tear strength so that the ceramic paper may be unwound from a roll by pulling on an unwound portion thereof. The ceramic paper should have a thermal conductivity less than about 2 BTU-in/hr.Ft.$^2$° F. at a mean temperature of 2000° F. An outer wrap is spirally wound around and confines the intermediate zone.

A tube in accordance with the present invention may be made at high speeds with low cost while producing unexpected results. It was unexpected that the ceramic paper containing a small amount of organic binder could be fed to a spiral tube machine and be unwound from a roll by pulling on an unwound portion at high speeds whereby tubing can be produced at a rate of in excess of 250 inches per minute. Tubes in accordance with the present invention have a variety of uses in connection with molten metal such as a non-splash thermocouple lance, a riser sleeve, ladle stopper rods, etc.

It is an object of the present invention to provide a novel composite high temperature protection tube which can be made inexpensively at high speeds.

It is another object of the present invention to provide a novel high temperature protection tube and method of making the same while using ceramic paper which is spirally wound as one zone of a composite tube.

Another objects and advantages will be set forth hereinafter.

For the purpose of illustrating the invention, there is shown in the drawings a form which is presently preferred; it being understood, however, that this invention is not limited to the precise arrangements and instrumentalities shown.

FIG. 1 is a sectional view through a tube in accordance with the present invention.

FIG. 2 is a diagrammatic plan view of a spiral tube machine utilized to produce the tube in FIG. 1.

FIG. 3 is a sectional view of a non-splash thermocouple lance incorporating the tube shown in FIG. 1.

FIG. 4 is a sectional view similar to FIG. 3 but showing an alternative construction for the mounting of the thermocouple in one end of the tube.

FIG. 5 is a sectional view through a portion of a stopper member which incorporates the concepts of the tube of the present invention.

Referring to the drawings in detail, wherein like numerals indicate like elements, there is shown in FIG. 1 a high temperature protection tube designated generally as 10. The tube 10 includes an inner core 12, an intermediate zone 14, and an outer wrap 16.

The inner core 12 as shown is a core of inexpensive spirally wound paperboard but may be made of other material such as spirally wound aluminum foil, plastic, or may be a metal tube such as steel or aluminum. When core 12 is made from a spirally wound material, the superimposed layers are bonded together with a bonding agent such as sodium silicate or colloidal silica. Core 12 is bonded to or otherwise supports zone 14.

The intermediate zone 14 is spirally wound layers of ceramic paper with the juxtaposed layers being bonded together with a bonding agent such as sodium silicate or colloidal silica. The ceramic paper is inorganic except for an organic binder in an amount sufficient to increase the tear strength so that the paper may be unwound from a roll by pulling on an unwound portion thereof. The ceramic paper is sold commercially with an organic binder present in an amount of 2.7 to 5% by weight. A suitable binder is neoprene latex. The ceramic paper should have a thermal conductivity less than about 2 BTU-in/hr.ft.$^2$° F. at a mean temperature of 2000° F. A preferred ceramic paper is ceramic paper No. 970-F sold commercially under the trademark FIBERFLAX by the Corborundum Company of Niagara Falls, New York and the preferred adhesive is type O sodium silicate, 42° Baume.

A typical chemical analysis of the ceramic paper, as per Carborundum publication A-2305, excluding the binder is as follows:

| | |
|---|---|
| $Al_2O_3$ | 51.7% |
| $SiO_2$ | 47.6% |
| $Na_2O$ | 0.3% |
| $B_2O_3$ | 0.15% |

| -continued | |
|---|---|
| Fe₂O₃ | 0.02% |
| Trace inorganics | 0.2% |
| Leachable chlorides | less than 50 parts per million |

The preferred ceramic paper has a white color, has a continous temperature limit use of 2300° F, a melting point of approximately 3300° F, fiber diameters of 2 to 3 microns, fiber length up to 1 inch, a density of 10 to 12 pounds per cubic foot, thermal conductivity of about 1.4 BTU-in./hr.Ft.$^{2°}$ F. at 2000° F, a specific gravity of 2.53 grams per cubic centimeter. The preferred ceramic paper having a rated thickness (measured at 8 psi compression in accordance with Tappi method T-411m44) of 0.040 inches weighs 0.053 pounds per square foot.

The outer wrap 16 is spirally wound around, is supported by, and confines the intermediate zone 14 to prevent the intermediate zone 14 from unwinding due to the long period of time necessary to attain a bond between the superimposed layers of the ceramic paper. The outer wrap 16 is preferably a layer of paper having a thickness of about 0.003 inches and is only a single layer thick. Other materials such as aluminum foil may be used for the outer wrap. It is unexpected that a single thickness of paper can be used for the outer wrap 16 and that it can perform the function of preventing the ceramic paper from unwinding while the adhesive forms a bond between the juxtaposed layers of the ceramic paper. Under typical production conditions, the layers of ceramic paper will be bonded together after sitting overnight at room temperature. As a result of the addition of the outer wrap 16, it is possible to make the tube 10 continuously at rates in excess of 250 inches per minute on a spiral tube machine.

In FIG. 2, there is diagrammatically illustrated a spiral tube machine 18. The machine 18 may be made in accordance with any one of a variety of commercially available equipment or in connection with the teachings of U.S. Pat. Nos. 2,623,443; 3,044,372 or 3,317,109. A typical spiral tube machine 18 includes a mandrel 20 which is continuously rotated in one direction by a motor 22. The mandrel 20 is unsupported at the end remote from the motor 22.

Referring to FIG. 2, a narrow web of material such as paperboard used for the core 12 is unwound from a roll 24, an adhesive bonding agent is applied to one surface, and then the web is wrapped around the mandrel 20. A narrow web of the ceramic paper is unwound from the roll 26, is coated on one surface with an adhesive bonding agent, and then spirally wrapped in the same direction around the core 12 while it is disposed on the mandrel 20. A narrow web of paper, aluminum foil or the like, is unwound from roll 28, coated on one side by an adhesive bonding agent, and then spirally wound in the same direction around the intermediate zone 14. In this manner, a composite spirally wound tube is continuously made and cut to unit lengths by flying cutter 30. Each of the narrow widths of material on the rolls 24, 26 and 28 is between 1⅜ and 2 inches wide.

The tube 10 has a variety of uses. For example, tube 10 may be used as part of an expendable non-splash thermocouple lance 32. In that regard, typical dimensions for tube 10 would be an ID of about 0.7 inches, an OD of about 1⅛ inches, a radial wall thickness of the inner core 12 of about 0.1 inches, a radial wall thickness of the intermediate zone 14 of about 0.1 inches, with the outer wrap 16 having a thickness of about 0.003 inches. Tube 10 is made in various lengths from 6 to 48 inches.

Referring to FIG. 3, a length of tube 10 is used as part of a non-splash expendable thermocouple lance 32. An expendable thermocouple body 34 is force-fit into the core 12 and has a shoulder that overlies an end face of the tube 10. A refractory or ceramic splice 36 is adhesively bonded to the outer periphery of one end portion of the tube 12 remote from the thermocouple body 34 and is also adhesively bonded to the outer periphery at one end of a spirally wound paper tube 38 concentric with and of the same dimensions as core 12.

When the lance 32 is immersed into a bath of molten metal, the outer wrap 16, when made of a single layer of paper, immediately disintegrates due to combustion. For a very short period of time, there is a small amount of bubbling due to the small amount of binder in the ceramic paper. The ceramic paper acts as an insulator for the core 12 made of paperboard whereby any residual moisture in core 12 (which is potentially hazardous) is slowly baked out of the core before any appreciable amount of heat is transmitted through the ceramic paper of intermediate zone 14 to the core 12 to thereby result in a paperboard core which is non-hazardous.

Instead of having the tube 10 of a short length coaxially attached to the extension tube 38, the tube 10 may have a length such as 18 inches to thereby assure that the immersed portion of the lance will be shorter than the length of tube 10. A metal support tube may be telescoped into the tube 10 for direct connection with the contacts on the inner end of the thermocouple body 34. If desired, the U-shaped tube containing the thermocouple hot junction may be protected by a conventional expendable cap.

If FIG. 4, there is illustrated another embodiment of a non-splash expendable thermocouple lance 32'. Lance 32' is the same as lance 32 except as will be made clear hereinafter. Before inserting a thermocouple body into the immersion end of the tube, the core 12 is reamed with a multidiameter reamer so as to completely remove a small portion of one end of the core 12 so as to produce an end face 40 while simulaneously reducing the inner diameter of a portion of core 12 as indicated at 42. The resultant reaming step produces a shoulder 44.

A thermocouple unit having an outer cylindrical sleeve 46 made from a material such as a paper tube or plastic tube with a refractory cement therewithin is inserted into the core 12 until the end cap 47 having plug-in connections rests on shoulder 44. The upper end of the refractory body 48 will then be contiguous with the end face 40 and the U-shaped tube 52 containing a hot junction will project beyond the end face of the lance 32'. Thereafter, refractory cement 50 will be added and permitted to solidify.

In FIG. 5, there is illustrated another embodiment of the present invention wherein the tube is designated 60. The tube 60 is adapted to be used an expendable stopper rod during the teeming of a ladle of hot molten metal. A typical stopper rod is designated by the numeral 12 in U.S. Pat. No. 2,893,860 and is comprised of a tube having a head on the lower end for performing a valving function and is surrounded by spaced ceramic sleeve-like elements. The tube 60 may also be used as a protection tube for devices which introduce solids or gases into a bath of molten metal.

The device 60 includes a core 62 which may be a metal tube or may be a spirally wound aluminum foil. Core 62 is surrounded by and supports an intermediate zone 64 of ceramic paper. Zone 64 is produced in the same manner as zone 14 described above. The intermediate zone 64 is surrounded by layers of spirally wound narrow strips of finely woven graphite cloth 66. The graphite cloth 66 forms a first heat barrier and the zone 64 forms a second heat barrier. The juxtaposed layers of the graphite cloth are bonded to each other and to the outer layer of zone 64. An outer wrap 68 of a single layer of paper or foil is spirally wound around the layers of graphite cloth. Wrap 64 corresponds to wrap 16.

When aluminum foil is used as the core, it also provides a vapor barrier, is a non-deteriorating inner wrap, is inexpensive, and can be wound on a spiral tube machine. Any one of the tubes disclosed herein may be used as pipe insulation. When device 60 is used as a ladle stopper, core 62 may be a steel tube which is bonded to the protection tube after being made on a spiral tube machine.

Thus, it will be noted that the tube of the present invention can be made more economically than protection tubes suggested heretofore while at the same time having a low thermal coefficient of conductivity, being light in weight, capable of being made at high speeds, is not brittle, and does not require baking at elevated temperatures. Since the tubes are shatterproof, no special care is required for handling or shipping.

The tubes of the present invention are surprisingly light in weight. One tube used commercially as a nonsplash thermocouple lance weights 0.044 lbs./in.; another weighs 0.036 lbs./in.; while tube 10 of the present invention only weighs 0.012 lbs/in. Thus, tube 10 is only one-third the weight of its closest competitor.

While use of a single layer of paper as the outer wrap 16 is contrary to accepted concepts for a high temperature protection tube capable of being immersed into molten steel, immediate destruction of wrap 16 upon contact with or exposure to a steel bath has no effect on use of the tube 10 wherein the inner core and zone 14 or components 64, 66 perform the protection function.

The present invention may be embodied in other specific forms without departing from the spirit or essential attributes thereof and, accordingly, reference should be made to the appended claims, rather than to the foregoing specification as indicating the scope of the invention.

We claim:

1. A composite high temperature protection tube, comprising:
   (a) an inner core of a first material,
   (b) an intermediate zone surrounding said core and being of a different material, said intermediate zone being supported by said core, said intermediate zone being spirally wound layers of ceramic paper bonded together, said ceramic paper being inorganic and having an organic binder in amounts sufficient to increase the tear strength thereof so that said ceramic paper may be unwound from a roll by pulling on an unwound portion thereof, said ceramic paper having a thermal conductivity less than 2 BTU-in./hr.Ft.$^2$° F. at a mean temperature of 2000° F,
   (c) an outer wrap bonded to itself along overlapping side edges and spirally wound around and confining said intermediate zone.

2. A tube in accordance with claim 1 wherein said first material is spirally wound paper tube, said outer wrap being a single layer of paper whose thickness is substantially less than the thickness of a layer of said ceramic paper.

3. A tube in accordance with claim 1 wherein one said first material and said outer wrap is aluminum foil.

4. A tube in accordance with claim 1 wherein said core is hollow and has a radial thickness substantially equal to the radial thickness of said intermediate zone.

5. A tube in accordance with claim 1 including an expendible temperature sensing unit at least partially disposed in and supported by an end portion of said tube.

6. A tube in accordance with claim 4 including a radially disposed shoulder on said core adjacent said one end portion of said tube, said sensing unit being in contact with said shoulder to orientate a sensing portion of said sensing unit a predetermined distance from an end face of said tube.

7. A tube in accordance with claim 6 wherein said unit includes a body whose axial length is less than the distance between said shoulder and said tube end face.

8. A tube in accordance with claim 1 including layers of spirally wound graphite cloth radially inwardly of said outer wrap but surrounding said layers of ceramic paper.

9. A method of making a composite high temperature tube comprising:
   (a) providing an inner core of a first material,
   (b) surrounding said core with a zone of a different material including spirally wound layers of ceramic paper having superimposed layers bonded together and being inorganic except for an organic binder in an amount sufficient to increase the tear strength of said paper, said step of surrounding said core including unwinding said ceramic paper in the form of a narrow strip from a roll with the axis of the the roll being at an acute angle with respect to a mandrel of a spiral tube machine,
   (c) confining said layers of said ceramic paper while on said mandrel by an outer wrap spirally wound therearound and bonded to itself along overlapped side edge portions,
   (d) cutting the thusly formed tube into unit lengths, and then
   (e) curing the bond between the juxtaposed layers of said ceramic paper while confined by said inner core and outer wrap.

10. A method in accordance with claim 9 wherein said step of providing an inner core includes spirally winding a narrow strip of core material on the mandrel of the tube machine and bonding overlapped juxtaposed edges of layers of the core strip to itself as said strip of ceramic paper is being spirally wound therearound.

11. A method in accordance with claim 10 including using a single layer of paper substantially thinner than the thickness of said ceramic paper as the outer wrap.

12. A method in accordance with claim 10 including using aluminum foil as one of said inner core and outer wrap.

13. A method in accordance with claim 10 including securing an expendable temperature sensing unit in one end of said tube after step (e).

* * * * *